United States Patent
Miethlinger et al.

(10) Patent No.: US 10,508,980 B2
(45) Date of Patent: Dec. 17, 2019

(54) MEASURING NOZZLE FOR DETERMINING THE EXTENSIONAL VISCOSITY OF POLYMER MELTS

(71) Applicant: Leistritz Extrusionstechnik GmbH, Nürnberg (DE)

(72) Inventors: Jürgen Miethlinger, Gampern (AT); Bernhard Löw-Baselli, Perg (AT); Hans Jürgen Luger, Linz (AT)

(73) Assignee: Leistritz Extrusionstechnik GmbH, Nürnberg (DE)

( * ) Notice: Subject to any disclaimer, the term of this patent is extended or adjusted under 35 U.S.C. 154(b) by 199 days.

(21) Appl. No.: 15/580,803

(22) PCT Filed: Jun. 7, 2016

(86) PCT No.: PCT/AT2016/050180
§ 371 (c)(1),
(2) Date: Dec. 8, 2017

(87) PCT Pub. No.: WO2016/197169
PCT Pub. Date: Dec. 15, 2016

(65) Prior Publication Data
US 2018/0231445 A1    Aug. 16, 2018

(30) Foreign Application Priority Data
Jun. 8, 2015   (AT) ............... A 50465/2015

(51) Int. Cl.
*G01N 11/08*   (2006.01)
*G01N 11/02*   (2006.01)
*G01N 11/04*   (2006.01)

(52) U.S. Cl.
CPC ............. *G01N 11/08* (2013.01); *G01N 11/02* (2013.01); *G01N 11/04* (2013.01)

(58) Field of Classification Search
CPC ........ G01N 11/00; G01N 11/02; G01N 11/04; G01N 2011/0026; G01N 2203/0094
See application file for complete search history.

(56) References Cited

U.S. PATENT DOCUMENTS

| 4,624,132 A | * | 11/1986 | Parnaby | ................. | G01N 11/08 |
| | | | | | 73/54.09 |
| 4,831,869 A | * | 5/1989 | Fowler | ................... | G01N 13/00 |
| | | | | | 73/150 A |

(Continued)

FOREIGN PATENT DOCUMENTS

| JP | 2003089917 A | 3/2003 |
| JP | 2004317471 A | 11/2004 |

OTHER PUBLICATIONS

Ober et al., "Microfluidic extensional rheometry using a hyperbolic contraction geometry", Rheologica Acta, Jun. 2013, available at rd.springer.com/article/10.1007/s00397-013-0701-y (Year: 2013).*

(Continued)

*Primary Examiner* — David A Rogers
(74) *Attorney, Agent, or Firm* — Tiajoloff & Kelly LLP; Andrew L. Tiajoloff

(57) ABSTRACT

The invention relates to a measuring nozzle for determining the extensional viscosity of polymer melts during their processing, comprising a flow channel which has a rectangular cross-section and which has a transitional section (3) between an inlet section (1) and an outlet section (2) with respective constant cross-section, which transitional section tapers hyperbolically in the flow direction (8) between two mutually opposite channel walls (6 and 7). In order to provide advantageous measuring conditions it is proposed that the transitional section (3) comprises an inlet-side zone (4) in which the mutual distance of the two channel walls (7) between the two hyperbolic channel walls (6) decreases continuously in the direction of flow (8), and an outlet-side (Continued)

zone (5) which adjoins the inlet-side zone and in which two of the channel walls (6, 7) disposed opposite one another in pairs extend parallel to one another, while the two channel walls (7) arranged therebetween converge hyperbolically in the flow direction (8).

2 Claims, 2 Drawing Sheets

(56) References Cited

U.S. PATENT DOCUMENTS

| | | | |
|---|---|---|---|
| 5,357,784 A | 10/1994 | Collier | |
| 5,499,869 A * | 3/1996 | Lauser | B29C 48/92 366/77 |
| 6,153,136 A * | 11/2000 | Collier | D01F 2/00 264/103 |
| 6,220,083 B1 * | 4/2001 | Collier | G01N 11/08 73/54.14 |
| 6,386,016 B1 * | 5/2002 | Gleissle | G01N 11/08 73/54.01 |
| 6,951,128 B2 * | 10/2005 | Odell | G01N 11/08 73/54.41 |
| 7,290,441 B2 * | 11/2007 | Baek | G01N 11/08 73/54.09 |
| 8,518,309 B2 * | 8/2013 | Maris-Haug | B29C 45/7646 264/328.1 |
| 8,652,852 B2 * | 2/2014 | Beebe | B01L 3/50273 422/50 |
| 2005/0183496 A1 * | 8/2005 | Baek | G01N 11/08 73/54.09 |
| 2008/0134765 A1 * | 6/2008 | Baek | G01N 11/08 73/54.09 |
| 2011/0215499 A1 * | 9/2011 | Luedeke | B29C 48/30 264/143 |
| 2019/0041311 A1 * | 2/2019 | Miethlinger | G01N 11/08 |

OTHER PUBLICATIONS

Chellamuthu et al., "Extensional rheology of shear-thickening nanoparticle suspensions", Soft Matter, vol. 5, 2009. (Year: 2009).*
Oliveira et al., "Newtonian fluid flow through microfabricated hyperbolic contractions,", Experiments in Fluids, Jan. 2008, available at www.researchgate.net/publication/285700257. (Year: 2008).*
Espacenet. English Language Abstract for JP 2004317471 (A) Nov. 11, 2004, Sanki Sangyo KK.
Espacenet. English Language Abstract for JP2003089917 (A) Mar. 28, 2003, Toray Industries.
R. Hidema et al., "Development of Extensional Viscosity Measurement Method on Low Viscos Polymer Solution with an Abrupt Contraction Flow", Japan Society of Mechanical Engineers: Collected Papers (B), Jul. 2013, 79, 803, 79-83.

* cited by examiner

MEASURING NOZZLE FOR DETERMINING THE EXTENSIONAL VISCOSITY OF POLYMER MELTS

FIELD OF THE INVENTION

The invention relates to a measuring nozzle for determining the extensional viscosity of polymer melts during their processing, comprising a flow channel which has a rectangular cross-section and a transitional section between an inlet section and an outlet section with respective constant cross-section, which transitional section tapers hyperbolically in the flow direction between two opposing channel walls.

DESCRIPTION OF THE PRIOR ART

A determination of the extensional viscosity by means of pressure sensors which are arranged upstream and downstream of a tapering of a flow channel of a measuring nozzle presupposes a constant mean strain rate of the polymer melt in the tapering section of the flow channel. For this purpose, it is known (U.S. Pat. Nos. 5,357,784, 6,220,083 B1) to provide a measuring nozzle with an inlet section and an outlet section, each of a constant cross-section, and with a transitional section tapering the inlet cross-section onto the outlet cross-section, which comprises two mutually opposite channel walls with a hyperbolic course for forming the tapering, but which otherwise has a rectangular cross-section between the converging channel walls and the channel walls extending parallel to one another, which channel walls converge with each other. As a result of this geometry of the transitional section between the inlet and the outlet section of the measuring nozzle, a largely constant mean strain rate can be ensured for the polymer melt, but with the disadvantage of a comparatively low pressure drop, which requires a high responsiveness of the pressure sensors used in the case of higher demands placed on the measuring accuracy. Apart from the fact that such pressure sensors are connected to the inflow and outflow sections of the flow channel via measuring capillaries drilled into the measuring nozzle, which entails the risk of deposits in these measuring capillaries, commercially available pressure sensors can hardly meet the requirements for measuring accuracy.

SUMMARY OF THE INVENTION

The invention is therefore based on the object of designing a measuring nozzle for determining the extensional viscosity of polymer melts in such a way that sufficient measuring accuracy can be ensured despite the use of commercially available pressure sensors.

On the basis of a measuring nozzle of the type described at the outset, the invention achieves the set problem in that the transitional section comprises an inlet-side zone in which the mutual distance of the two channel walls between the two hyperbolic channel walls decreases continuously in the direction of flow, and an outlet-side zone which adjoins the inlet-side zone and in which two of the channel walls disposed opposite one another in pairs extend parallel to one another, while the two channel walls arranged therebetween converge hyperbolically in the flow direction.

As a result of the division of the transitional section into an inlet-side zone in which, with respect to the channel walls disposed opposite each other in pairs, one pair continuously converges the other pair hyperbolically in the flow direction and while maintaining the flow conditions for a constant mean strain rate, and an outlet-side zone in which a pair of the channel walls disposed opposite each other in pairs also converge hyperbolically, while the other pair has a constant mutual distance, an extension of the flow section is enabled in which a constant average strain rate prevails. This leads to an increase in the pressure loss, on the basis of which the extensional viscosity is calculated, thus providing the design prerequisites for the use of commercially available pressure sensors which can meet higher requirements for the measuring accuracies despite a moderate responsiveness in connection with the measuring nozzle according to the invention.

The geometrical prerequisites for a measuring nozzle according to the invention permit the direct connection of commercially available pressure sensors at least to the inlet-side section of the flow channel via a connecting thread. If the parallel channel walls of the outlet-side zone of the transitional section delimit the width of the flow channel so that no change in the width of the flow channel results after the tapering of the channel width in the inlet-side zone, commercially available pressure sensors can also be connected directly to the flow channel in the outlet-side section of the measuring nozzle while avoiding measurement capillaries of commercially available pressure sensors.

BRIEF DESCRIPTION OF THE DRAWING

The subject matter of the invention is shown by way of example in the drawings, wherein.

DESCRIPTION OF THE PREFERRED EMBODIMENT

Figure 1:
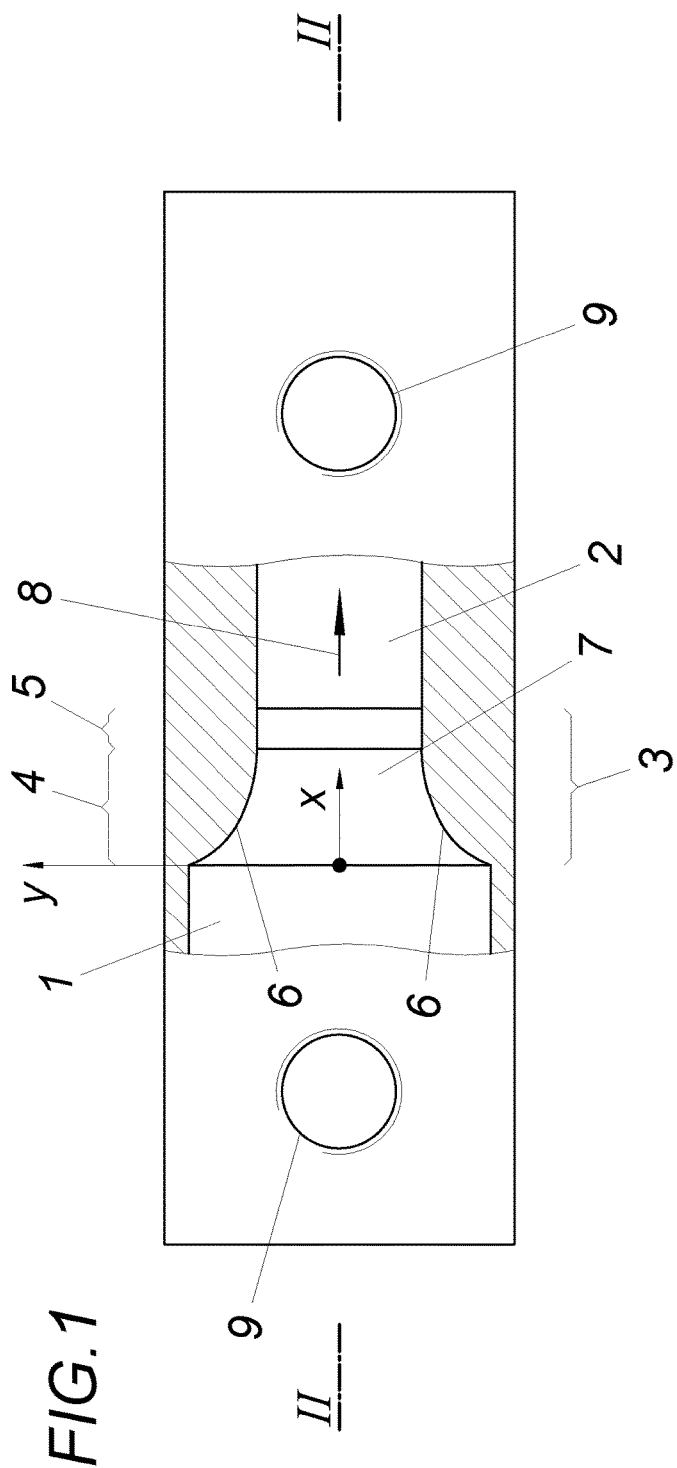
FIG. 1 shows a measuring nozzle according to the invention for determining the extensional viscosity of polymer melts in a schematic, partially broken-away top view.
Figure 2:
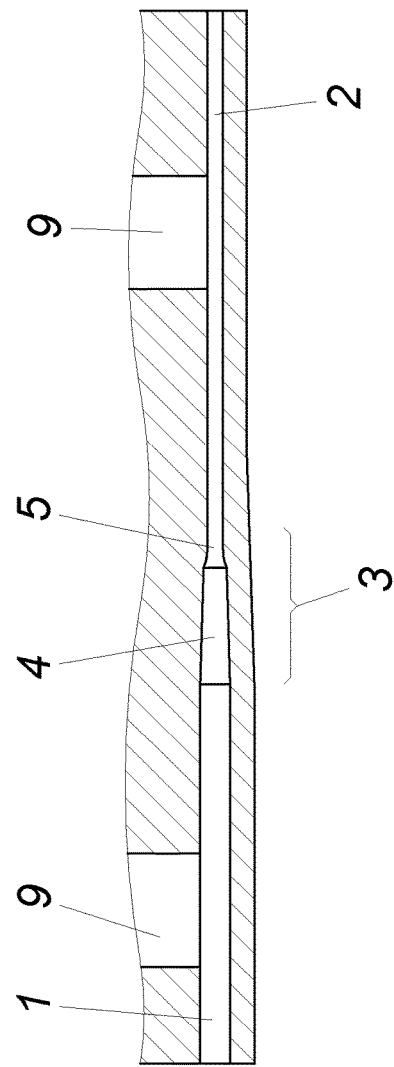
FIG. 2 shows this measuring nozzle in a section along the line II-II of FIG. 1.
Figure 3:
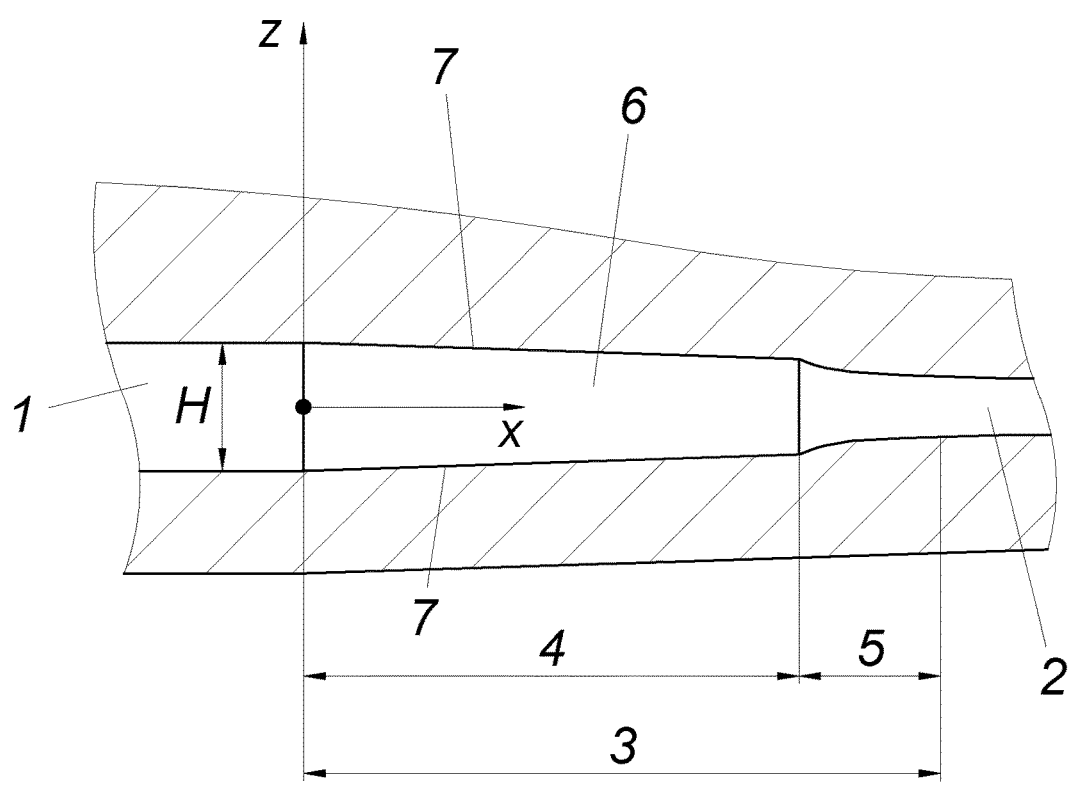
FIG. 3 shows the transitional section between the inlet and the outlet section of the measuring nozzle in a longitudinal section on a larger scale.

The illustrated measuring nozzle forms a flow channel for a polymer melt which comprises an inlet section 1 which can be connected, for example, to an extruder, and an outlet section 2, as well as a transitional section 3 between the inlet and outlet section 1, 2. The flow cross-section is continuously rectangular throughout the nozzle length. In the transitional section 3, the flow cross-section of the inlet section 1 is reduced to the cross-section of the outlet section 2, which is reduced both with respect to width and height compared to the inlet section 1, namely under flow conditions which ensure a constant mean strain rate in the transitional section 3. For this purpose, the transitional section 3 is subdivided into an inlet-side zone 4 and an outlet-side zone 5 with different respective geometric form. In the inlet-side zone 4, two channel walls 6 of the channel walls 6, 7 which are opposite one another in pairs converge hyperbolically, while the mutual spacing of the channel walls 7 of the other channel wall pair decreases steadily in the flow direction 8, preferably linearly. In order to obtain a constant mean strain rate in the inlet-side zone 4, the width y of a rectangular cross-section, at the position x in the nozzle longitudinal direction, must satisfy the condition $$y = C/(a + k_1 x) \cdot z$$

wherein C, a and $k_1$ are constants dependent on flow conditions, and z is the half-height of the cross-section at the position x. In the case of a linear decrease in the height, $z=H/2-k_2 x$ is obtained when a central X axis and a height H of the cross-section of the inlet-side section 1 and a slope $k_2$ for the inclination of the relevant channel wall 7 in relation to the nozzle axis is assumed, as indicated in FIGS. 1 and 3.

A pair of the channel walls 6, 7 is guided in parallel in the adjoining, downstream-side zone 5 in order to maintain a constant mean strain rate, while the other pair converges in the flow direction 8 according to a hyperbolic function. In the exemplary embodiment, the channel walls 7 which determine the height of the flow channel converge such that no reduction in the channel width results from this channel tapering in the region of the zone 5. This circumstance makes it possible to connect commercially available pressure sensors directly to the flow channel, not only in the area of the inlet section 1, but also in the area of the outlet section 2. In the exemplary embodiment, this is indicated by connection bores 9.

Due to the particular geometric shape of the measuring nozzle, the length range of the transitional section 3 is increased in comparison with known measuring nozzles, by being able to maintain a constant mean strain rate as a prerequisite for the determination of the extensional viscosity of polymer melts. The associated increase in the pressure drop makes the measuring nozzle more sensitive so that sufficiently accurate measuring results can be obtained even with commercially available pressure sensors.

The invention claimed is:

1. A measuring nozzle for determining the extensional viscosity of polymer melts during their processing, said nozzle comprising:
   a flow channel having a rectangular cross-section and a transitional section between an inlet section and an outlet section each having a respective constant cross-section,
   wherein said transitional section tapers hyperbolically in a flow direction between pairs of opposing channel walls,
   wherein the transitional section comprises
   an inlet-side zone in which the pairs of said channel walls each have a respective distance therebetween that decreases continuously in the direction of flow, and the channel walls of one of the pairs of said opposing channel walls is hyperbolic in shape,
   an outlet-side zone that adjoins the inlet-side zone and in which the two channel walls of one of the pairs of the channel walls disposed opposite one another extend parallel to one another, and the two channel walls of the other of the pairs of channel walls arranged therebetween converge hyperbolically in the flow direction.

2. A measuring nozzle according to claim 1, wherein the parallel channel walls of the outlet-side zone of the transitional section delimit the width of the flow channel.

\* \* \* \* \*